(12) United States Patent
Overes et al.

(10) Patent No.: US 10,413,423 B2
(45) Date of Patent: Sep. 17, 2019

(54) EXPANDABLE SPINAL IMPLANT

(71) Applicant: 41MEDICAL AG, Bettlach (CH)

(72) Inventors: Tom Overes, Langendorf (CH); Robert Frigg, Bettlach (CH)

(73) Assignee: 41MEDICAL AG, Bettlach (CH)

( * ) Notice: Subject to any disclaimer, the term of this patent is extended or adjusted under 35 U.S.C. 154(b) by 200 days.

(21) Appl. No.: 15/463,248

(22) Filed: Mar. 20, 2017

(65) Prior Publication Data
US 2017/0266015 A1    Sep. 21, 2017

(30) Foreign Application Priority Data
Mar. 21, 2016  (CH) ..................... 00386/16

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/30382* (2013.01); *A61F 2002/30556* (2013.01); *A61F 2002/30579* (2013.01); *A61F 2002/4475* (2013.01)

(58) Field of Classification Search
CPC .......... A61F 2/44; A61F 2/4455; A61F 2/447; A61F 2002/4475
See application file for complete search history.

(56) References Cited

U.S. PATENT DOCUMENTS

| 6,685,742 | B1 | 2/2004 | Jackson |
| 8,685,095 | B2* | 4/2014 | Miller ................. A61F 2/447 623/17.11 |
| 9,814,602 | B2* | 11/2017 | Faulhaber ............ A61F 2/447 |
| 10,022,241 | B2* | 7/2018 | Faulhaber ............ A61F 2/447 |
| 2010/0286783 | A1 | 11/2010 | Lechmann et al. |

(Continued)

FOREIGN PATENT DOCUMENTS

| EP | 1 941 847 A1 | 7/2008 |
| WO | 2005/112834 A2 | 12/2005 |

(Continued)

OTHER PUBLICATIONS

Written Opinion of the International Searching Authority dated Apr. 7, 2016 as received in Application No. PCT/CH2015/000106.

*Primary Examiner* — Eric S Gibson
(74) *Attorney, Agent, or Firm* — Maschoff Brennan

(57) ABSTRACT

An expandable spinal implant assembly for insertion between two adjacent vertebral bodies includes a first body with a first superior endplate and a first inferior endplate, which are connected together. A strut is comprised by said first body and connects with one of said endplates, said strut including a first threaded through bore with a central axis. The spinal implant assembly further includes a substantially hollow second body having a second superior endplate and a second inferior endplate, and is engaged within said first body. At least one track is arranged on a second top inside face of said second superior endplate and/or on a second bottom inside face of said second inferior endplate, said track being oriented at an acute angle relative to the central axis of said first threaded through bore when said substantially hollow second body is at least partially engaged with said first body.

14 Claims, 10 Drawing Sheets

(56) References Cited

U.S. PATENT DOCUMENTS

| | | | |
|---|---|---|---|
| 2012/0215316 A1* | 8/2012 | Mohr | A61F 2/442 623/17.16 |
| 2012/0259416 A1* | 10/2012 | Blackwell | A61F 2/4455 623/17.16 |
| 2012/0310350 A1* | 12/2012 | Farris | A61F 2/4425 623/17.16 |
| 2013/0103156 A1* | 4/2013 | Packer | A61F 2/442 623/17.16 |
| 2013/0110243 A1* | 5/2013 | Patterson | A61F 2/4455 623/17.16 |
| 2013/0158668 A1* | 6/2013 | Nichols | A61F 2/4455 623/17.16 |
| 2013/0190876 A1* | 7/2013 | Drochner | A61F 2/442 623/17.16 |
| 2013/0282122 A1* | 10/2013 | Ullrich, Jr. | A61F 2/4465 623/17.16 |
| 2014/0052253 A1 | 2/2014 | Perloff et al. | |
| 2014/0180419 A1 | 6/2014 | Dmuschewsky | |
| 2015/0012098 A1* | 1/2015 | Eastlack | A61F 2/447 623/17.15 |
| 2016/0331542 A1* | 11/2016 | Faulhaber | A61F 2/447 |

FOREIGN PATENT DOCUMENTS

| | | |
|---|---|---|
| WO | 2013/184946 A1 | 12/2013 |
| WO | 2014/091028 A1 | 6/2014 |
| WO | 2016/049784 A1 | 4/2016 |

\* cited by examiner

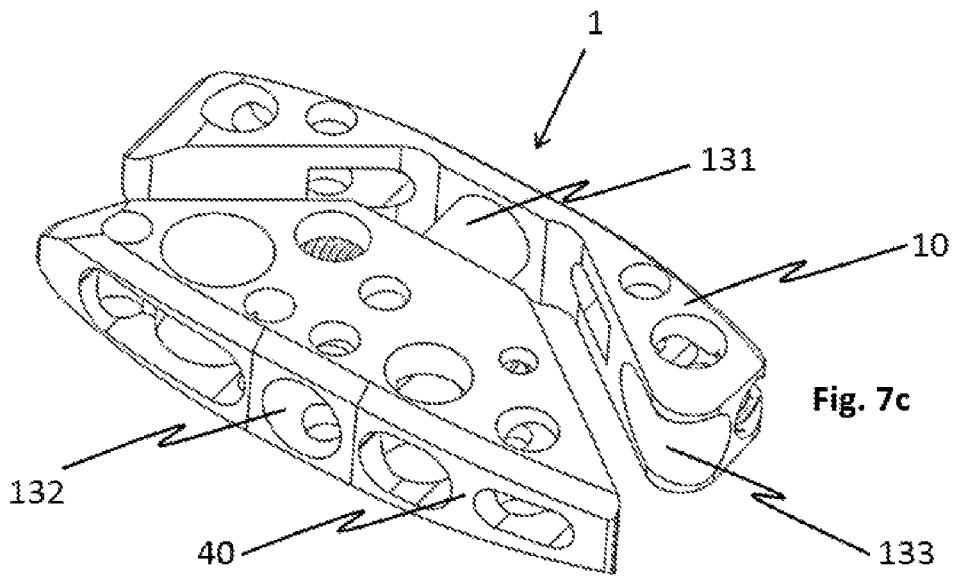
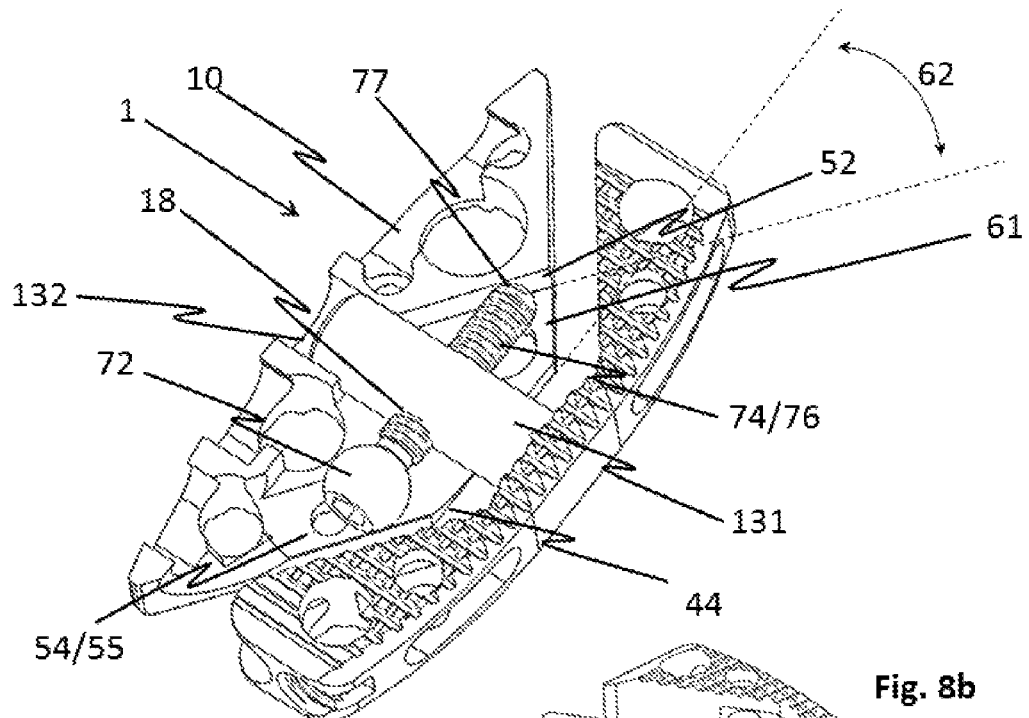
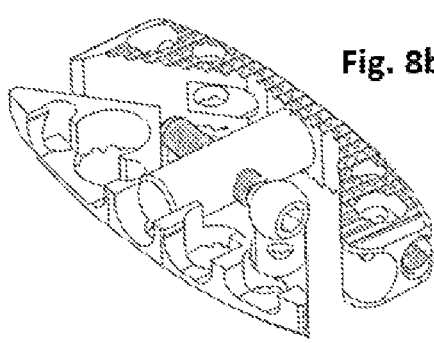

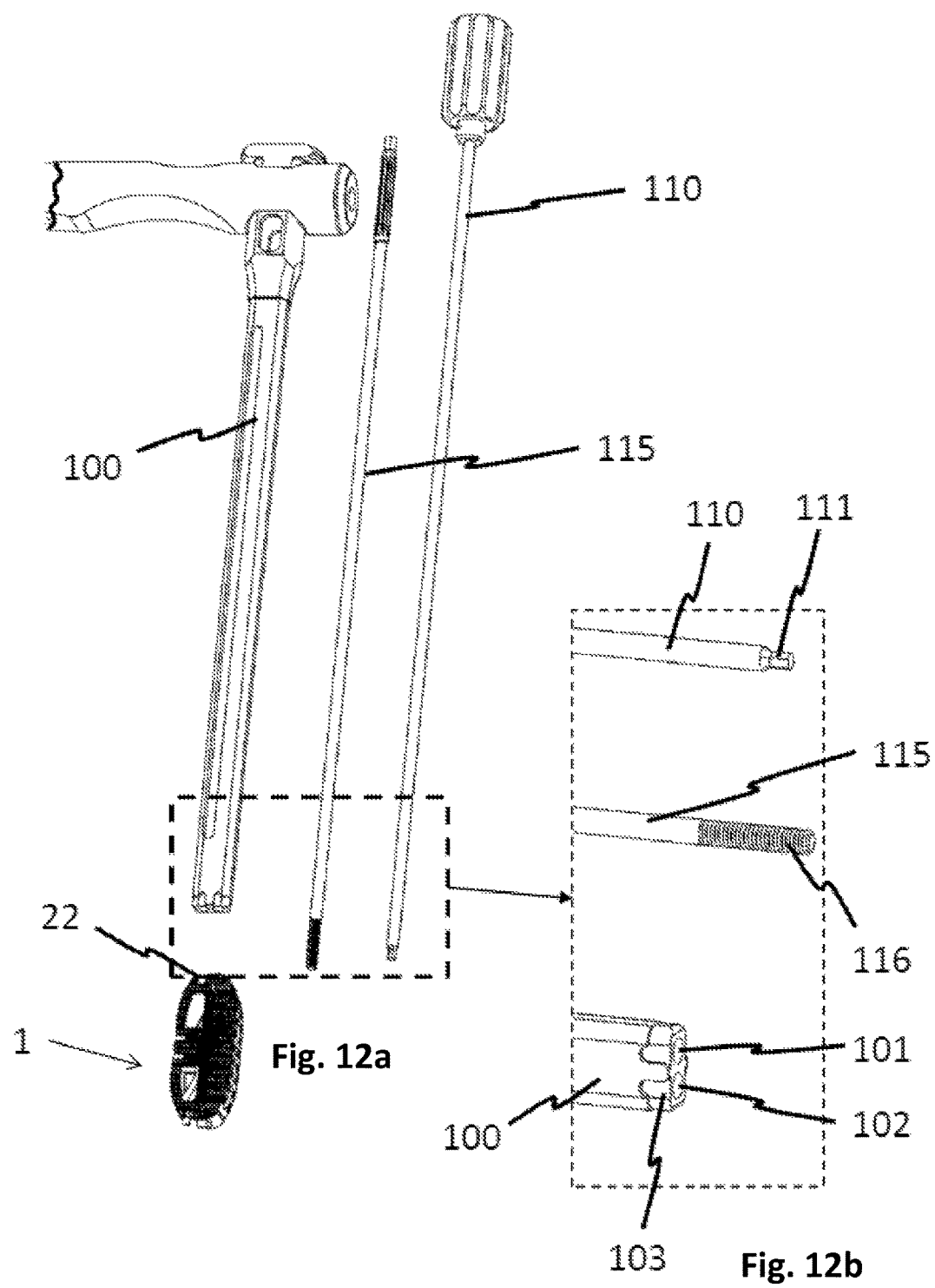

EXPANDABLE SPINAL IMPLANT

TECHNICAL FIELD

The invention relates to an expandable spinal implant assembly.

BACKGROUND ART

Low back pain is a common disease which may be caused by herniated discs, compressed nerve roots, degenerative discs or joint disease.

If a patient suffers severe low back pain and does not respond to conservative treatment, spinal fusion is an option to eliminate the pain. Spinal fusion is a surgical technique wherein two or more vertebrae are joined together. Spinal fusion interventions are also performed to correct back deformities.

With spinal fusion, often an intervertebral spacer or device is placed between the involved vertebrae after removal of the intervertebral disc. The intervertebral device corrects the spine alignment and restores the disc height. Common intervertebral devices are made from titanium alloys or PEEK (polyetheretherketone) polymer. Often these devices comprise pockets that can be filled with bone graft material or artificial graft substitute. The fusion itself takes place when the bone of the vertebral endplates grows into and through the intervertebral device. Finally both vertebrae are grown together. Often, a pedicle system provides additional posterior stabilisation. Intervertebral fusion devices can be implanted with various approaches, for example with an anterior, posterior or lateral approach.

Over the past years minimally invasive techniques have been introduced. One advantage of the minimal invasive techniques is a reduction of soft tissue trauma resulting in a faster recovery. Other complications are reduced as well. In minimally invasive techniques the implant is brought into position between the vertebral bodies through a small incision with small instruments. However, the intervertebral device must still have a sufficient large foot-print to withstand the forces between the vertebrae before complete fusion has taken place. If a device has a too small foot-print it will sink into or break through an endplate of a vertebra, and the initially restored height is lost.

Combining advantages of the minimally invasive surgery approaches with intervertebral devices with large footprint affording a good support would require a device which may be brought into place through a small incision and which in a second step may be expanded to a larger size.

SUMMARY OF THE INVENTION

It is the object of the invention to create an expandable spinal implant assembly which may be implanted in a first, collapsed configuration with small dimensions and which may be transformed into a second, expanded configuration with a larger footprint by simple means. Further, the expandable spinal implant assembly should be easily collapsible in the event that the expandable spinal assembly has to be removed.

The solution of the invention is specified by the features of claim 1. According to the invention the expandable spinal implant assembly for insertion between two adjacent vertebral bodies comprises:

a) a first body with a first superior endplate and a first inferior endplate;
b) at least one strut extending from or within said first body, and being connected with said first superior endplate and first inferior endplate, said strut comprising a first threaded through bore with a central axis;
c) a substantially hollow second body with a second superior endplate and a second inferior endplate, said second body being at least partially engaged with said first body;
d) a central screw with a first end comprising a ball-head and a drive, said central screw further having a threaded shaft which is arranged to be engaged within said first threaded through bore, wherein at least one track is arranged on a second top inside face of said second superior endplate and/or on a second bottom inside face of said second inferior endplate, said at least one track being oriented at an acute angle relative to the central axis of said first threaded through bore when said substantially hollow second body is at least partially engaged with said first body, wherein said ball-head of said central screw is engaged in said at least one track, and wherein the surface roughness of at least one of said ball-head, threaded shaft or at least one track is at most 25 micrometers.

With the arrangement of the ball-head within the at least one track, the expandable spinal implant assembly may be moved from a first, collapsed configuration into a second, expanded configuration having a larger footprint than said first configuration. I.e. the simple rotation movement of the central screw is transformed into a translation movement of the second substantially hollow body relative to the first body. Hence, a very simple yet effective mechanism for the expansion of the spinal implant assembly is established.

Both said first body and said second body may be "substantially hollow". In the present application, "substantially hollow" is understood as a body having a defined shape which comprises a void space between the superior endplate and the inferior endplate, wherein said void may comprise at least one element spanning between said superior endplate and said inferior endplate, e.g. in the form of the at least one strut. Said superior endplate and said inferior endplate are connected together by at least one wall on a side face of said first implant body or said second implant body. At least one side face of both said first body and said second substantially hollow body does not comprise a wall or comprise an passage such as to allow access to the central screw from the outside of the expandable spinal implant. Substantially hollow can further be defined by pockets, cut outs through the bodies as well as voids between the endplates of the bodies. Spinal fusion implants preferably have a very open structure to allow for bone ingrowth and through-growth.

The "endplates" of the first body are those faces of the expandable spinal implant assembly which are positioned to bear against the vertebral bodies once the expandable spinal implant assembly is implanted.

The expandable spinal assembly may have a generally rectangular shape. Alternatively, said superior and said inferior endplates of both said implant bodies are generally oval in shape, wherein the front face is preferably straight. In an alternative embodiment the spinal assembly has a generally rectangular shape with rounded or chamfered edges.

The expandable spinal assembly hence has six faces. The upper and the lower faces are those faces which will bear against the endplates of the upper and the lower vertebral bodies, respectively, once implanted. Further, the expandable spinal assembly has an anterior and a posterior face. The posterior face is on the side of the expandable spinal implant assembly which will face towards the spinous process of the vertebra once implanted. Consequently, the anterior face is the side which will be oriented towards the torso of a patient. Additionally, the expandable spinal assembly comprises a front face and a back face. The front face is located on the side of the implant which is oriented towards a surgeon during an implantation of the expandable spinal assembly via a lateral approach.

The back face is located on the side of the implant which is opposite the front face.

The strut may only partially span along one dimension of the first body within said void space between the first superior endplate and the first inferior endplate. The strut may be arranged to be essentially parallel to the front side of said expandable spinal implant assembly.

The drive of the central screw is intended to be engaged with a surgical instrument, such as a screw driver. Hence, the drive preferably is in the form of a slot, Phillips drive, hex socket, Torx drive or the like. The drive hence serves to transmit torsional moment from a surgical instrument to the central screw such as to entail a rotational movement of the central screw.

The at least one track is oriented at an acute angle relative to the central axis of said first threaded through-bore. An "acute angle" as used in the present application is understood to be an angle of less than 90° but more than 0°. By providing a track having an acute angle relative to the central axis of the first threaded through bore, a translational movement of the central screw along said central axis is transformed in a translational movement of the substantially hollow second body relative to the first body by the engagement of the ball head of the central screw into said at least one track. Preferably, said first body and/or said second body comprise means to guide said translation in a direction which is perpendicular to said central axis of the first threaded through bore.

Said acute angle of said at least one track relative to said central axis of the first through bore may be such that the at least one track is inclined in an anterior to posterior direction as seen from the front side. Hence, a translation of the central screw towards the rear side will result in an increase of the footprint of the expandable spinal implant assembly, as the second body is pushed out of the void between the endplates of the first body towards the expanded configuration.

Alternatively, the acute angle of said at least one track relative to said central axis of the first through bore is such that the at least one track is inclined in a posterior to anterior direction as seen from the front side. In this variant, the expansion of the expandable spinal implant assembly is achieved by a translation of the central screw towards the front side.

By varying the acute angle of the at least one track relative to the central axis of the first threaded through bore and/or the thread pitch of said first threaded through bore and said central screw, the translation speed of said second body relative to said first body may be varied.

The expandable spinal assembly may include a superior track located on said second top inside face of said second superior endplate and an inferior track located on said second lower inside face of said second inferior endplate, said superior track and said inferior track being arranged symmetrically to each other and forming a cylindrical channel.

In this embodiment of the present invention, the ball head of the central screw is engaged in both said superior track and said inferior track. Said superior track and said inferior track may have the same centre and radius, e.g. they both form an arc of the same cylindrical channel. This allows an easy manufacture of said superior and said inferior tracks, as they may be made using a drill. Preferably, the radius of said cylindrical channel is marginally larger than a maximal radius of the ball head.

The acute angle of said at least one track relative to said central axis of the first threaded through bore may be between 5° and 45°, or more specifically between 10° and 30°. By using angles within said range, an optimal translational speed of said second body relative to said first body may be achieved.

Further, the force with which the expandable spinal implant assembly expands is related to the angulation of the acute angle. The lower the angle is, the larger the exerted force of the expandable spinal implant assembly will be.

The strut may comprise a second threaded through bore substantially parallel to said first threaded through bore for engagement with a coupling core of an insertion instrument. This allows to couple said expandable spinal implant assembly with an insertion instrument by means of e.g. a threaded coupling core. In an alternative embodiment the second threaded through bore is arranged in the front side of the first body.

A first front side of said first implant body may comprise a recess in said first superior endplate and said first inferior endplate. Said recess may be arranged parallel to a second central axis of said second through bore for forming a connection means with the insertion instrument. Said recess and said second threaded through bore may intersect.

By providing said recess, the expandable spinal implant assembly may be connected with the insertion instrument in an angle stable manner, i.e. any rotation of the expandable spinal implant assembly around an axis of the insertion instrument is prevented by the engagement of the insertion instrument with said recess.

In one embodiment, the second body has a height which is smaller than the distance between the first top inside face and the first bottom inside face of the first body. This allows the second body to be at least partially inserted into the first body. Preferably, the difference between the first distance D1 and the second distance D2 is selected such that the second superior endplate and the second inferior endplate engage with the first top inside face and the first bottom inside face, respectively, while allowing a gliding motion of the endplates relative to the inside faces. For example, the first distance D1 may be 0.2 mm greater than the second distance D2.

The ball head of said central screw is preferably a cylindrical head, a conical head or a double conical head. These shapes of the ball head provide a good interaction with the at least one track, especially in cases where the at least one track is provided in the form of an arc of a cylindrical channel. The second body preferably comprises at least one second track arranged on a second top inside face of said second superior endplate and/or on a second bottom inside face of said second inferior endplate, said at least one second track being oriented parallel relative to the central axis of said first through bore.

Said at least one second track may be arranged such as to be co-axial with the central axis of the first threaded though bore when said expandable spinal implant assembly is in the first, collapsed configuration. Hence, the central screw may be easily inserted and removed when the expandable spinal implant assembly is in the first, collapsed configuration.

The strut may comprise a first portion connecting the first top inside face of the superior endplate with the first bottom inside face of the inferior endplate and a second strut portion, of cylindrical shape, extending therefrom. The second body may comprise a guiding bore for receiving said second cylindrical portion.

In an alternative embodiment the second strut portion is of rectangular shape, rectangular shape with blended edges, or rectangular shape with chamfered edges. Respectively the second body comprises passage, sized and shaped to receive said second strut portion. Advantages of a rectangular shape are the provision of the rotational stability of said first body in relation to said second body. Disadvantages of a rectangular shape may be the manufacturability.

In an alternative embodiment the strut is an integral element of the posterior face of the expandable spinal implant.

This allows a further guiding of a translation of the first body relative to the second body when said expandable spinal implant assembly is moved from the first, unexpanded configuration to the second, expanded configuration or vice versa.

In this embodiment, the first threaded through bore is preferably located in said second strut portion.

Said ball head of said central screw has a second diameter and said elongated shaft of said central screw has a third diameter, wherein the ratio between said second diameter and said third diameter may be at least 110:100, or more specifically at least 130:100. A higher ratio of the ball head in relation to said elongated shaft provides an improved force transfer in said tracks.

The expandable spinal implant assembly has a first footprint in the first, unexpanded configuration and a second footprint in the second, expanded configuration, wherein the ratio between said first footprint and said second footprint may be at least 100:125.

In the present application, the term "footprint" is understood as the area of a vertebra covered by said expandable spinal implant assembly, i.e. an area which corresponds to the product of the first length L1 and the first width W1 or the second width W2, respectively.

Hence, in this preferred embodiment, the footprint in said second, expanded configuration is at least 25% larger than in said first, unexpanded configuration. It is to be noted that said increase in footprint is mediated uniquely by an increase of the width of the expandable spinal implant assembly, while the first length L1 does not vary between said first, unexpanded configuration and said second, expanded configuration.

Said spinal implant assembly has a first length L1 and said central screw has a third length L3, wherein the ratio between said first length L1 and said third length L3 is smaller than 100:80, or more specifically smaller than 100:70.

With this ratio, it may be ensured that the central screw will not protrude from the expandable spinal implant assembly in the second, expanded configuration, while the third length L3 is sufficient to provide enough translational movement of the central screw within said first threaded through bore and hence of the ball head within said at least one track to ensure an efficient expansion of the expandable spinal implant assembly from the first, unexpanded configuration to the second, expanded configuration.

Said first element, said second element and said central screw may be made of titanium, a titanium allow, stainless steel or a biocompatible polymer, preferably polyetheretherketone (PEEK). With the arrangement of the ball-head within the at least one track, the expandable spinal implant assembly may be moved from a first, collapsed configuration into a second, expanded configuration having a larger footprint than said first configuration. I.e. the simple rotation movement of the central screw is transformed into a translation movement of the second substantially hollow body relative to the first body. For a smooth transformation of forces and prevention of causing debris due to friction, a smooth surface roughness is needed. Purposefully the surface roughness of said ball-head and said track is at most 5 micrometers and preferably at most 0.8 micrometers. Surface roughness Ra may be measured in two ways: contact and non-contact methods. Contact methods involve dragging a measurement stylus across the surface; these instruments are called profilometers. Non-contact methods include: interferometry, confocal microscopy, focus variation, structured light, electrical capacitance, electron microscopy and photogrammetry.

The endplates and/or protrusions, configured to engage with the vertebral bodies, may be of different roughness, preferably a rougher roughness. In an alternative embodiment the endplates comprise a rough and porous and open structure. A possible manufacturing technique for said porous and open structure is additive manufacturing such as selective laser melting of titanium powders. Other exemplary additive manufacturing techniques may be selective laser melting, selective laser sintering, electro beam melting, selective heat sintering, 3D printing, etc.

Surface roughnesses with a high porosity allow for a high bone ingrowth.

A further aspect of the present application is to provide a kit comprising at least two expandable spinal implant assemblies according to the present invention. The at least two expandable spinal implant assemblies differ in at least one of the following: the first length L1, a first width W1 in the unexpanded configuration, a second with W2 in the expanded configuration, the first distance D1, the second distance D2, a first inclination angle and/or a second inclination angle of said first upper endplate relative to said first lower endplate or of said second upper endplate relative to said second lower endplate, respectively.

Such a kit allows a surgeon to choose the best fitting expandable spinal implant assembly for a patient.

A further aspect of the present application is to provide a method for spinal fusion using an expandable spinal implant assembly according to the present invention. Said method comprises as a first step the removal of an intervertebral disc between two adjacent vertebrae. Various methods on how to remove a vertebral disc are known to a person having skill in the art. In a second step, an expandable spinal implant assembly according to the present invention is placed between said two adjacent vertebrae in the first, collapsed configuration. Said first, collapsed configuration has a first footprint. Afterwards, the expandable spinal implant assembly is expanded to the second, expanded configuration by rotation of the central screw, e.g. by means of a screw driver or power tool. The second, expanded configuration has a second footprint which is larger than said first footprint.

Preferably, the placement of said expandable spinal implant assembly is performed using an insertion instrument which is coupled to said expandable spinal implant assembly by means of a threaded tip of a coupling core of said insertion instrument threadably engaged with a second through bore of said expandable spinal implant assembly. Other advantageous embodiments and combinations of features come out from the detailed description below and the totality of the claims.

BRIEF DESCRIPTION OF THE DRAWINGS

The drawings used to explain the embodiments show:

FIGS. 7a-7c different perspective views of an alternative embodiment of the expandable spinal implant according to the present invention;

FIGS. 8a, 8b the interaction of all individual components of the expandable implant assembly according to the second embodiment in perspective views with partial cross sections;

FIGS. 12a, 12b an insertion instrument used in connection with an expandable spinal implant assembly according to the present invention.

In the figures, the same components are given the same reference symbols.

DETAILED DESCRIPTION OF EMBODIMENTS OF THE INVENTION

Figure 1A:
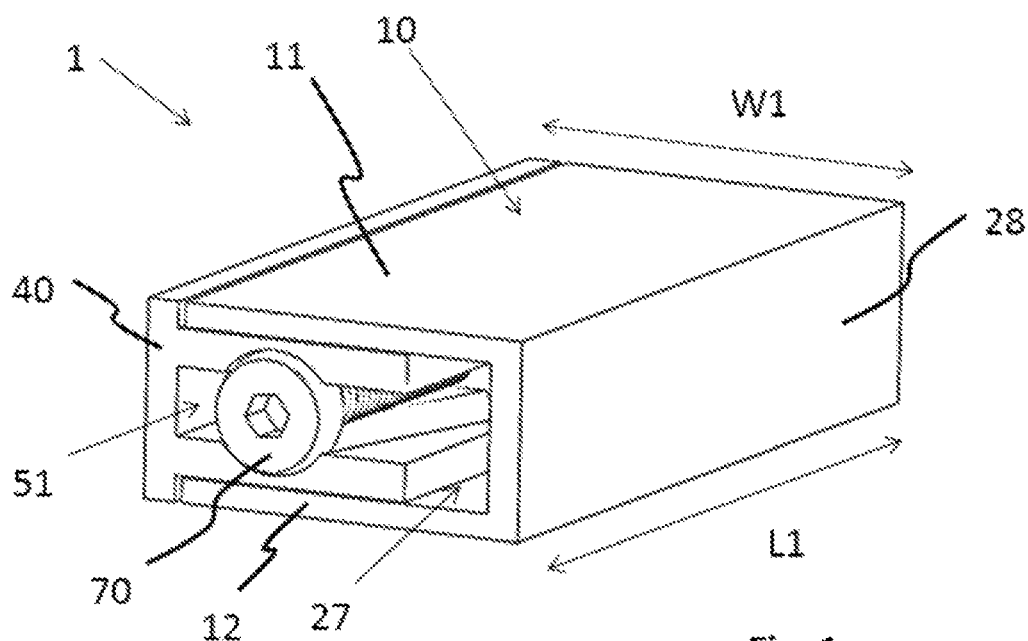
FIGS. 1a, 1b a perspective representation of a first embodiment of an expandable spinal implant assembly according to the present invention.
Figure 1B:
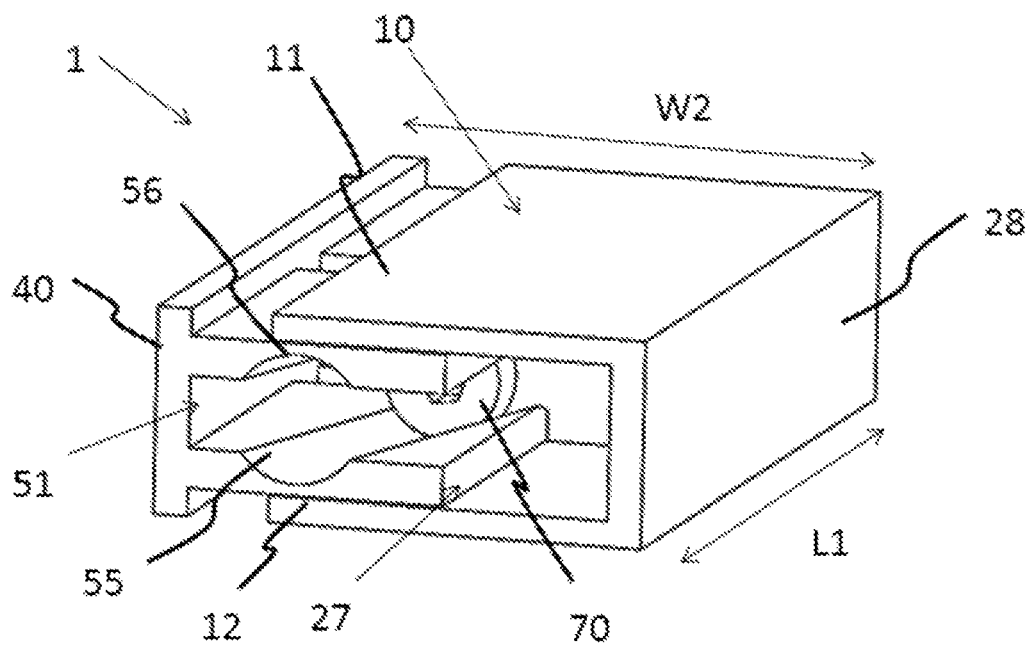

FIGS. 1a and 1b show a perspective representation of a first embodiment of an expandable spinal implant assembly 1. In FIG. 1a, the expandable spinal implant assembly 1 is in a first, collapsed configuration. In this configuration the expandable spinal implant assembly 1 has a first footprint surface area defined by a first width W1 and a first length L1.

FIG. 1b shows the expandable spinal implant assembly 1 in a second, expanded configuration. In said second configuration, the expandable spinal implant assembly 1 has a second footprint surface area defined by a second width W2 and the first length L1. The second width W2 is larger than said first width W1.

The expandable spinal implant assembly comprises a first body 10. The first body 10 includes a first superior endplate 11 and a first inferior endplate 12. Said first endplates 11, 12 are connected together by a first side plate 28. Between said two first endplates 11, 12 and said first side plate 28 the first body 10 comprises a first void 27.

Further, the expandable spinal implant assembly 10 comprises a substantially hollow second body 40. Said second body 40 includes a second superior endplate 41 and a second inferior endplate 42. Both said second endplates 41, 42 are connected together by a second side plate 48. Between said two second endplates 41, 42 and said second side plate 48 the substantially hollow second body 40 comprises a second void 51.

The expansion of the expandable spinal implant assembly 1 is caused by a translation of the first body 10 relative to the second body 40. This translation results in an increase of the overall width of the expandable spinal implant assembly 1 from the first width W1 to the second width W2.

Translation of the two bodies 10, 40 relative to each other is caused by a translation of a central screw 70 in a direction which is substantially perpendicular to the translation direction of the second body relative to the first body. A ball head 71 of said central screw 70 is engaged in a cylindrical channel defined by two tracks 55, 56 arranged opposite each other on the inside of said second body 40 and being configured to have an acute angle relative to said central screw 70. When said central screw 70 is rotated, a threaded engagement of said central screw 70 will cause a translation of the central screw 70 along said two tracks 55, 56. As the two tracks 55, 56 include an acute angle in relation to the central screw 70, the translation of the central screw 70 within the two cylindrical channels 55, 56 will cause a translational movement of said substantially hollow second body 40 relative to said first body 10.

Figure 2A:
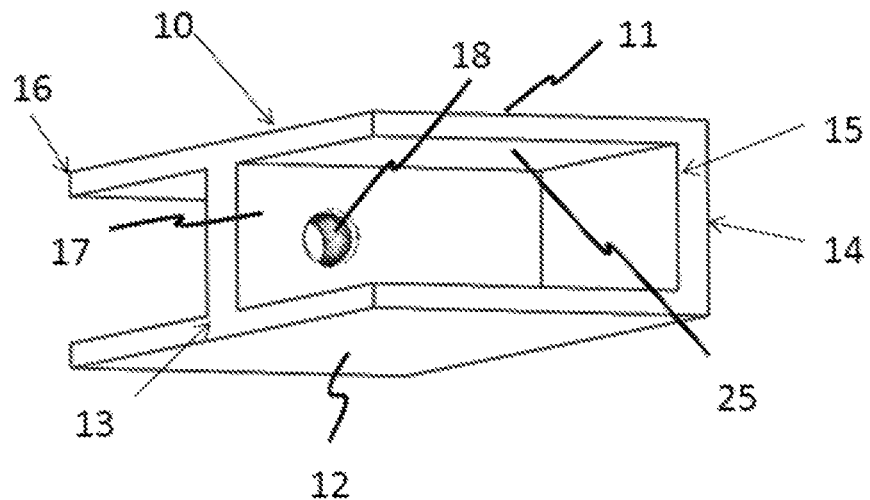
FIGS. 2a, 2b different perspective views of the first body according to the first embodiment.
Figure 2B:
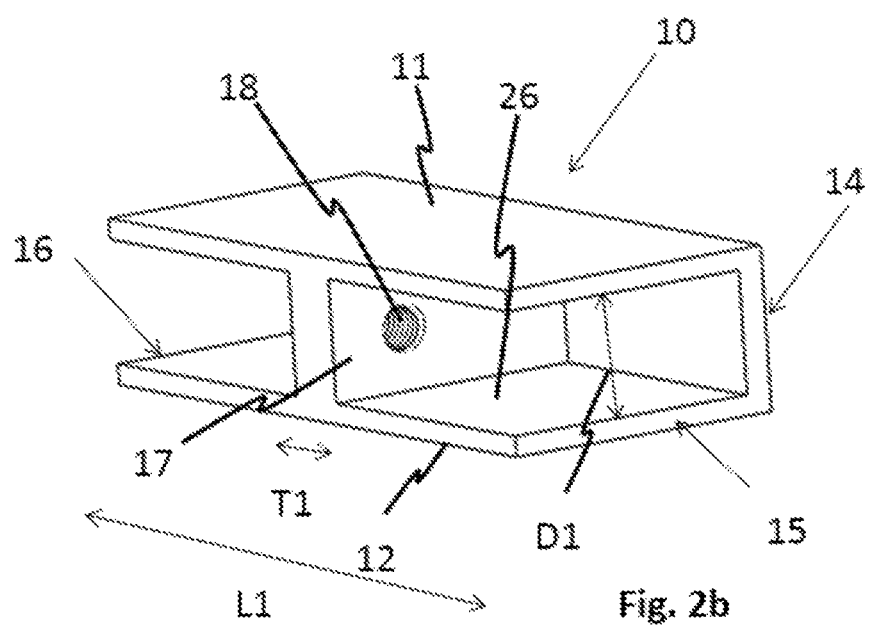

FIGS. 2a and 2b show different perspective views of said first body 10. The first body 10 comprises a first superior endplate 11 and a first inferior endplate 12. The first body 10 has a first anterior end 13, a first posterior end 14, a first front side 15 and a first rear side 16. The first superior endplate 11 and the first inferior endplate 12 define a first inner top face 25 and a first inner bottom face 26, respectively. A strut 17 is arranged between said first inner top face 25 and said first inner bottom face 26, spanning from said first posterior end 14 to said first anterior end 13. The strut has a first thickness T1 which is oriented in the direction from the first front side 15 to the first rear side 16. The first superior end plate 11 and the first inferior endplate 12 are connected by the strut 17 and by the first side plate 28, which spans between said first endplates 11, 12 along said posterior end 14 of the first body 10. The strut 17 is located substantially centrally between said first front side 15 and said first rear side 16. The strut 17 comprises a first threaded through bore 18. The first threaded through bore 18 is intended for engagement with said central screw 70.

Figure 3A:
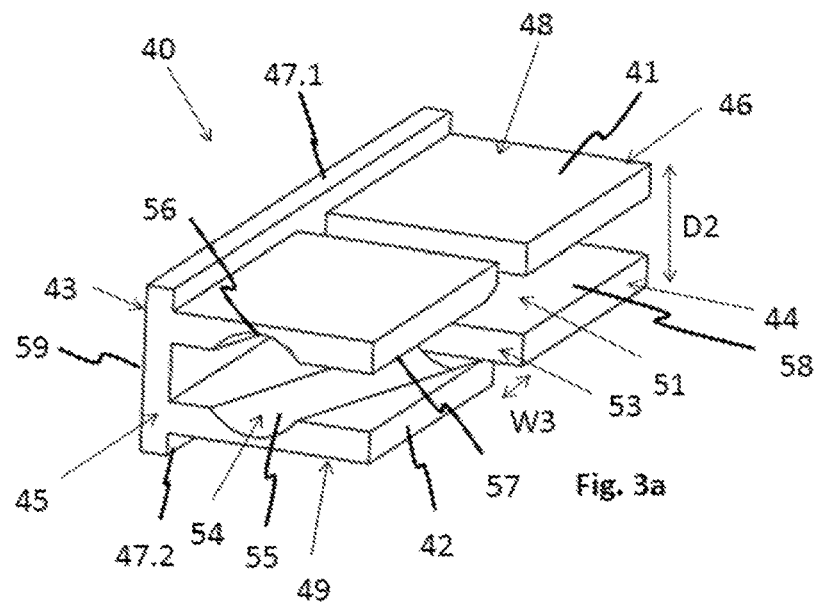
FIGS. 3a, 3b different perspective views of the second body according to the first embodiment.
Figure 3B:
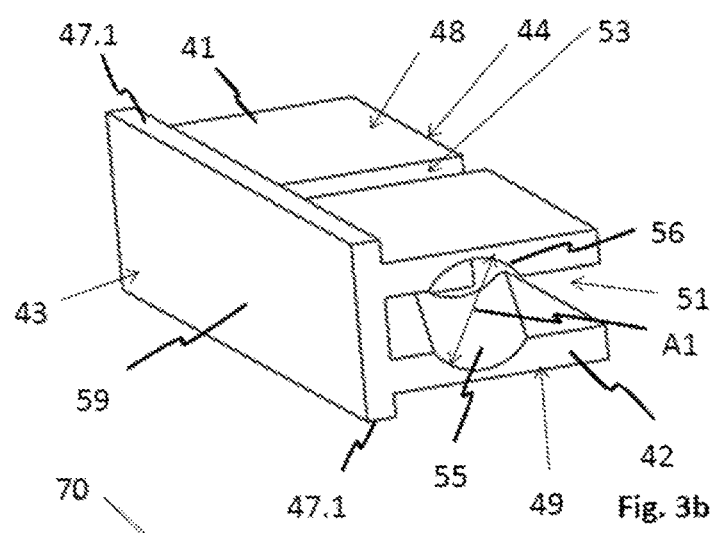

FIGS. 3a and 3b show the second body 40 in different perspective views. The second body 40 comprises a second superior endplate 41 and a second inferior endplate 42 located at a second top side 48 and a second bottom side 49, respectively. Further, the second body 40 has a second anterior end 43, a second posterior end 44, a second front side 45 and a second rear side 46. The second superior endplate 41 and the second inferior endplate 42 are parallel to each other and include a second void 51 between each other. The second superior endplate 41 and the second inferior endplate 42 are spaced from each other by a second distance D2.

The second endplates 41, 42 are joined together at the second anterior end 43 by a second side plate 59. The second side plate 59 is dimensioned such as to extend over the second superior endplate 41 and the second inferior endplate 42, such as to form two protrusions 47.1, 47.2 on said second top side 48 and said second bottom side 49. Said protrusions 47.1, 47.2 are dimensioned to substantially extend to the level of the first superior endplate 11 and the first inferior endplate 12, respectively, of the first body 10 when said second body 40 is at least partially inserted into said first body 10.

The second superior endplate 41 and the second inferior endplate 42 comprise a guiding recess 53 extending from the second posterior end 44 to the second side plate 59. Said guiding recess 53 has a third width W3, wherein said third width W3 is substantially equal to the first thickness T1 of the strut 17 of the first implant body 10.

Further, a cylindrical channel 54 with a first diameter A1 is defined by a superior track 55 located on a surface of a second top inside face 57 of the second superior endplate 41 facing towards the second void 51 and by an inferior track 56 located on a surface of a second bottom inside face 58 of the second inferior endplate 42 facing towards the second void 51. The tracks 55, 56 extend from said second front side 45 towards said guiding recess 53. The tracks 55, 56 form an acute angle with the second front side 54. Once the second body 40 is at least partially inserted into the first body, the tracks 55, 56 will include an acute angle relative to the axis of the first trough bore 18.

Figure 4:
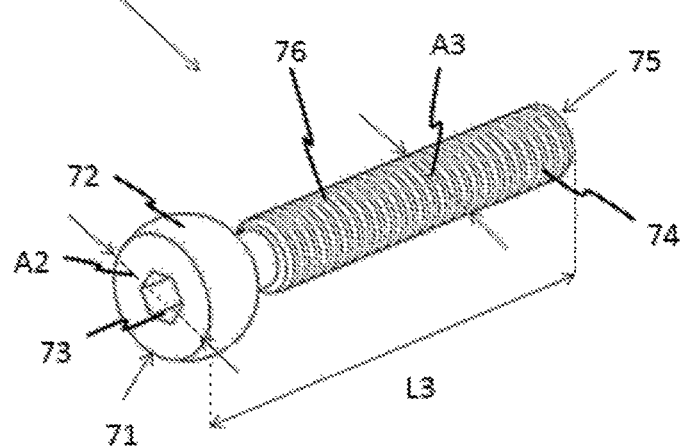
FIG. 4 a detailed representation of the central screw.

FIG. 4 shows the central screw 70 in greater detail. The central screw 70 has a first end 71 with a ball-head 72. The ball-head 72 includes a drive 73 and has a second diameter A2. The second diameter A2 is substantially equal to the first diameter A1 of the cylindrical channel 54 of the second body 40. The central screw 70 furthermore comprises an elongated shaft 74 extending from said first end 71 to a second end 75.

The elongated shaft 74 is a threaded shaft having an outer screw thread 76 and a third diameter A3. The central screw 70 has a third length L3. The third length L3 spans the entire elongated shaft 74 as well as the ball-head 72. In this embodiment, the ratio between the second diameter A2 and the third diameter A3 is larger than 110:100, or more specifically larger than 130:100. With a large ratio between the second diameter A2 and the third diameter A3 the transfer of translational forces between the central screw 70 and the cylindrical channel 54 is enhanced.

In this example, the ratio between the first length L1 of the expandable spinal implant assembly 1 and the third length L3 of the central screw 70 is smaller than 100:80, or more specifically smaller than 100:70.

Figure 5A:
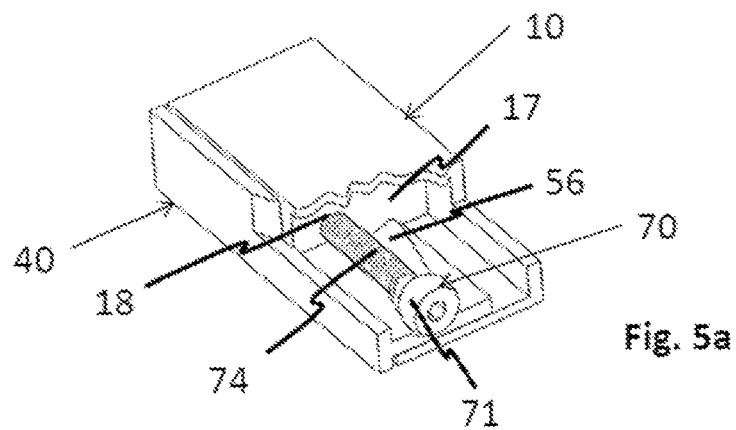
FIGS. 5a-5c the interaction of all individual components of the expandable implant assembly according to the first embodiment in perspective views.
Figure 5B:
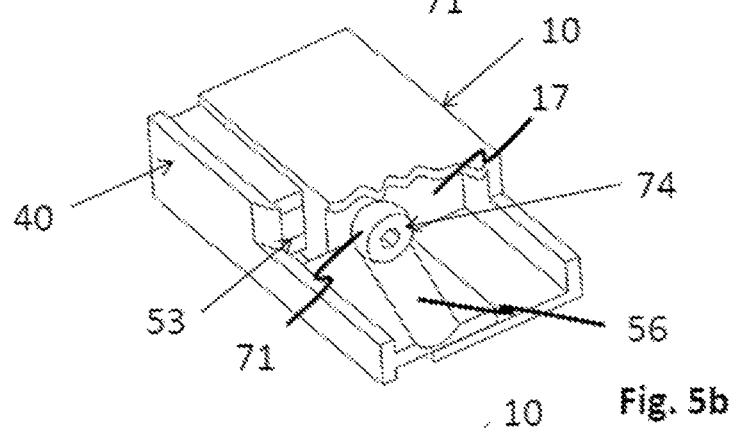
Figure 5C:
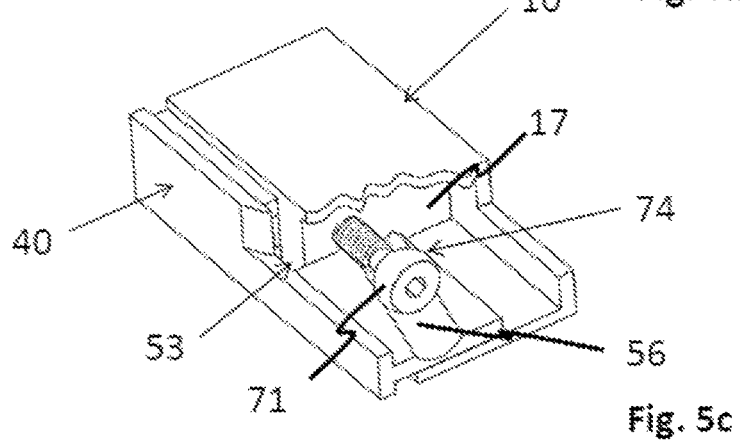

FIGS. 5a to 5c show the interaction of all individual components of the expandable implant assembly 1 in perspective views. The first body 10 and the second body 40 are shown in a partial cross-sectional view.

FIG. 5a depicts the expandable implant assembly 1 in a first, collapsed configuration. The elongated shaft 74 of the central screw 70 is engaged into first threaded through bore 18 of the strut 17 of the first body 10. Simultaneously, the ball-head 72 of the central screw 70 is engaged within the superior track 55 and the inferior track 56 of the second body 40. The strut 17 is arranged within the guiding recess 53. This restricts the movement of the bodies 10, 40 relative to each other to the direction of the recess 53 and prevents any motion of the bodies 10, 40 relative to each other in any other direction. Further, the interaction of said first top inside face 25 with the second superior endplate 41 and the interaction of the first bottom inside face 26 with the second inferior endplate 42 prevents any vertical or angular motion of the two bodies 10, 40 relative to each other.

FIG. 5b shows the expandable implant assembly 1 in a second, expanded configuration. Upon rotation of the central screw 70, e.g. by means of an instrument coupled to the drive 73, a linear motion will be imparted on said central screw 70 by the interaction of the outer thread 76 on the elongated shaft 74 with the first threaded through bore 18. The engagement of the ball head 72 within the tracks 55, 56 leads to a transfer of this motion onto the second body 40. As the tracks 55, 56 form an angle with the second front side 54 as well as with the axis of the first through bore 18 and the second body 40 is blocked of moving in the translational direction of the central screw 70 relative to the first body 10 by the engagement of the guiding recess 53 with said strut 17, the linear motion of the ball head 72 within the first threaded through bore 18 is transformed into a translational motion of the substantially hollow bodies 10, 40 relative to each other in a direction which is perpendicular to the axis of said through bore 18 by the engagement of the ball head 72 within said tracks 55, 56. As a result, by rotating the central screw 70, the second body 40 is pushed relative to the first body 10 towards the second, expanded configuration.

Often in surgery, an implant must be removed. Therefore any implant that can expand must be collapsible as well. FIG. 5c shows the collapsing of the expandable spinal implant assembly 1 from the second, expanded configuration towards the first, collapsed configuration. Upon unscrewing of the central screw 70, the ball head 72 is moved towards the first front side 15 of the first implant body 10. The ball-head 72 located in the tracks 56, 57 will exert a force upon said substantially second hollow body pulling said second body 40 back into the first void 27 of said first body 10.

Thus, with the arrangement of the ball-head within the at least one track, the expandable spinal implant assembly may be moved from a first, collapsed configuration into a second, expanded configuration having a larger footprint than said first configuration. I.e. the simple rotation movement of the central screw is transformed into a translation movement of the second substantially hollow body relative to the first body. For a smooth transformation of forces and prevention of causing debris due to friction, a smooth surface roughness is needed. Purposefully the surface roughness of said ball-head and said track is at most 5 micrometers, or more specifically at most 0.8 micrometers. Surface roughness Ra may be measured in two ways: contact and non-contact methods. Contact methods involve dragging a measurement stylus across the surface; these instruments are called profilometers. Non-contact methods include: interferometry, confocal microscopy, focus variation, structured light, electrical capacitance, electron microscopy and photogrammetry.

Figure 6:
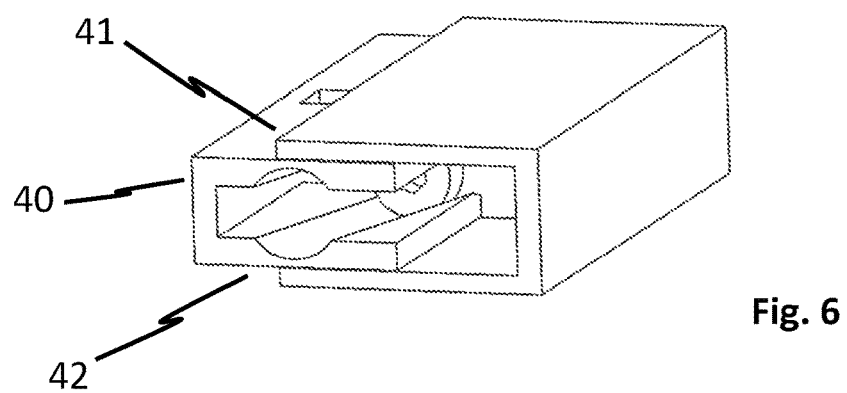
FIG. 6 an alternative embodiment of the expandable spinal implant as depicted in FIGS. 1 to 5.

FIG. 6 shows an alternative embodiment of the expandable spinal implant assembly 1. The second substantially hollow body 40 has a second superior endplate 41 and second inferior endplate 42. At least one of second endplates forms the primary engagement surface for direct engagement against the target vertebral body. In a preferred embodiment, the distance between said second endplates 41,42 defines the largest height of the second body 40. In comparison to said expandable spinal implant as described in connection with FIGS. 1 to 5, at least one top or bottom side of the second body 40 does not comprise said protrusion 47.1, 47.2.

Figure 7A:
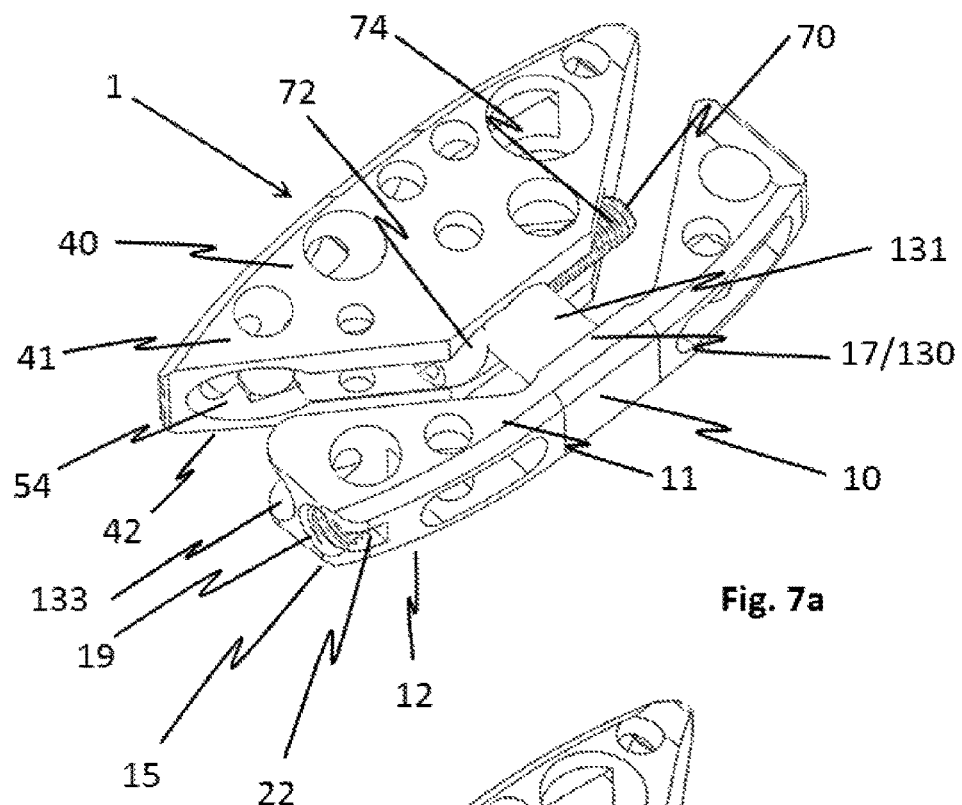
Figure 7B:
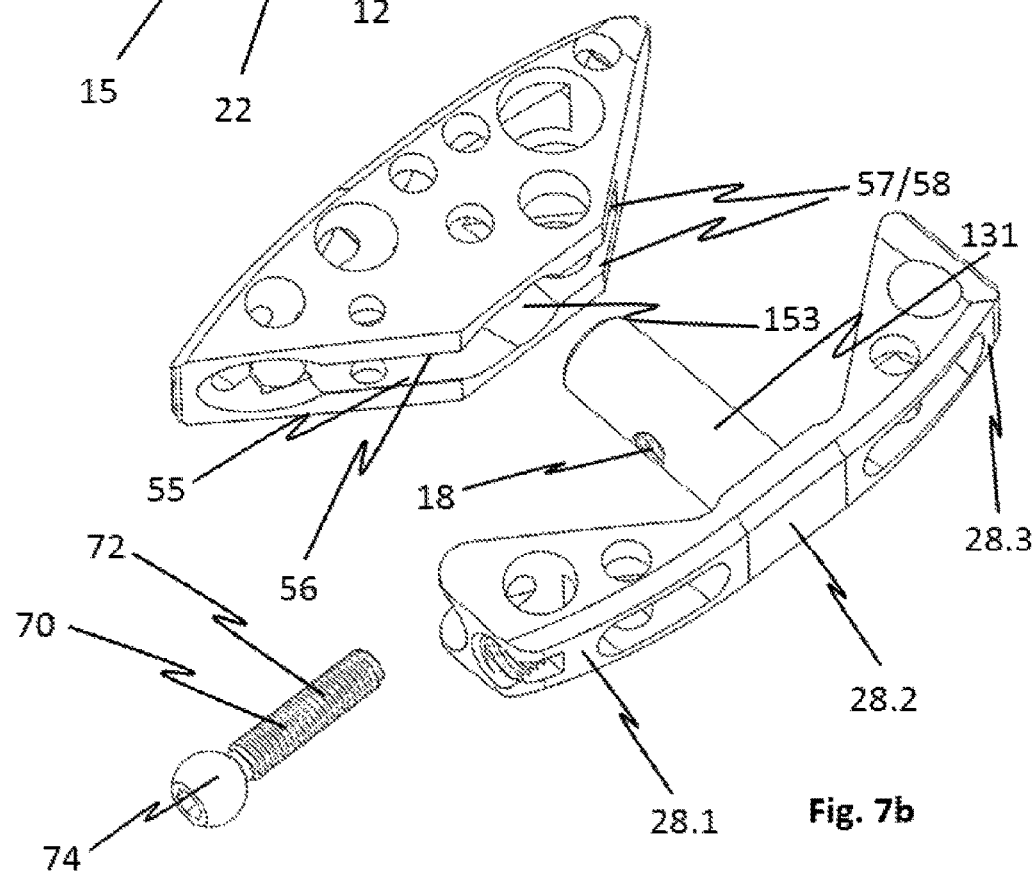

FIGS. 7a to 7c show a further embodiment of the expandable spinal implant assembly 1 in a perspective view and an exploded view. For illustration purposes the implant assembly shown does not comprise a rough structure for bone ingrowth, which functionality is explained in greater detail later.

The second body 40 comprises a guiding bore 132. In an example embodiment, the first body 10 and the second body 40 have complementary, substantially V-shaped sides which match together when the expandable spinal implant assembly 1 is in the first, unexpanded configuration. The complementary V-shapes of said first body 10 and said second substantially hollow body 40 form a substantially compact, closed form in the unexpanded configuration of the expandable spinal implant assembly. This compactness provides a maximal engagement surface when expanded. This engagement surface may comprise pockets as explained later. Upon expansion, the complementary V-shape is opened, providing a large open space between the first body 10 and the second body 40. Said large open space allows for insertion of a large amount of bone grafting material to promote the fusion of the vertebral bodies.

In an alternative embodiment, the complementary shape may be a W-shape or U-shape.

The expandable implant assembly as depicted in FIGS. 7a to 7c comprises the first body 10 with the first superior endplate 11 and the first inferior endplate 12, and further comprising the second body 40 with the second superior endplate 41 and the second inferior endplate 42. Due to complementary overall shape of said first body 10 and second body 40, said second endplates 41, 42 are not inserted between the first endplates 11, 12 from said first body 10. In this embodiment, said first and second superior endplates are substantially flush and aligned with each other, and likewise the first and second inferior endplates are substantially flush and aligned with each other.

The strut 17 of the first body 10 comprises a first portion 130 connecting the first top inside face of the superior endplate 11 with the first bottom inside face of the inferior endplate 12 and a second portion 131 of cylindrical shape extending therefrom. Said strut may be an integral element of the posterior face of the expandable spinal implant. The first threaded through bore 18 is located in said second portion 131. The second cylindrical portion 131 is sized and shaped to engage into the guiding bore 132 of the second body 40. Hence, in this embodiment, the translation of the first body 10 relative to the second body 40 from the first, unexpanded configuration to the second, expanded configuration is guided by the interaction of the second portion 131 of the strut 17 with said guiding bore 132.

Because the second portion 131 of the strut is of cylindrical shape, said first body and second body can rotate in relation to each other, if only said first and second body are considered. In combination with the central screw 70 this rotational degree of freedom may be blocked. In one example, said central screw 70 comprises a ball-head 72 which is engaged in said at least one of superior track 55 and inferior track 56 of said substantially hollow second body 40. Simultaneously said elongated shaft 74 is engaged inside the first threaded through bore 18. The combination of engagements of said elongated shaft and said ball-head prevent rotation of said first body 10 in relation to said second body 10.

A further rotation inhibiting means of said expandable spinal implant assembly may be the engagement of said elongated shaft between said second superior endplate 41 and second inferior endplate 42 of said second substantially hollow implant body 40, in combination with engagement of said elongated shaft 74 of said central screw in said first threaded through bore 18. Said elongated shaft 74 may be sized and shaped to engage with said second top inside face 57 and second bottom inside face 58 of respectively said second superior endplate 41 and second inferior endplate 42.

In one example, said central screw 70 is simultaneously engaged with said tracks 55, 56 and said second top inside face 57 and second bottom inside face 58, wherein said ball-head 72 and elongated shaft 74 are sized and shaped to mate with said tracks and inside faces with minimal play.

The simultaneous engagement of the ball-head 72 with said superior track 55, and elongated shaft 74 with second top inside face 57, would inhibit rotation of said first body 10 in relation to said second body 40.

Hence, also the simultaneous engagement of the ball-head 72 with said inferior track 56, and said elongated shaft 74 with said second bottom inside face 58, would inhibit rotation of said first body 10 in relation to said second body 40.

In order to allow the insertion and assembly of the central screw 70 into said expandable spinal implant assembly 1, a partial round opening 133 is provided on the first front side 15 of the first body 10.

Further, the second threaded through bore 19 and a recess 22 are provided on the first front side 15 of the first body 10. The second threaded through bore 19 and recess 22 allow the angle stable coupling of the expandable spinal implant 1 with an insertion instrument.

FIG. 7b shows a substantially hollow first body 10 in an exploded view from the first posterior end 14. In contrast to the first embodiment as shown in FIGS. 1 to 5, the first side plate 28 is replaced by multiple support struts 28.1, 28.2, 28.3. Each support strut 28.1, 28.2, 28.3 transfers loads exerted on the first superior endplate 11 to the first inferior endplate 12 and vice versa. The position, shape and size of the support struts 28.1, 28.2, 28.3 may also vary. The support struts 28.1, 28.2, 28.3 are configured for an optimal load transfer, but are preferably as small as possible to provide as much space as possible for bone in and over-growth, which finally causes the spinal vertebral bodies to fuse. The position, shape and size of the support struts 28.1, 28.2, 28.3 may also vary depending on the chosen manufacturing technique, such as for example milling, wire EDM for titanium implants, or milling and injection moulding for PEEK implants.

FIGS. 8a and 8b show detailed views of the spinal implant assembly 1 with a section-cut through the second body 40. The second void 51 comprises angled slope 52. The angled slope 52 is arranged in a posterior recess 61 which spans from said second superior endplate 41 to said second inferior endplate 42. The angled slope 52 is arranged at a third inclination angle 62 relative to the second posterior end 44.

The cylindrical channel 54 has the first diameter A1 and extends from the second front side 45 towards the guiding bore 132. As for the first embodiment, the cylindrical channel 54 is defined by the superior track 55 and the inferior track 56 (not shown due to the section-cut). The superior track 55 and the inferior track 56 are circular in shape and share the identical centre and radius. Alternatively at least one of the tracks 55, 56 may have a quadratic or triangular shape. In a preferred embodiment the angled slope 52 and said tracks 55, 56 are parallel.

The elongated shaft 74 of the central screw 70 is engaged into the first threaded through bore 18 of the first body 10. Simultaneously, the ball head 72 of the central screw 70 is engaged and captured into the superior track 55 and the inferior track 56 forming the cylindrical channel 54 of the second body 40. The conical tip 77 of the central screw 70 engages against the angled slope 52 of the second body 40.

When a turning motion is imparted on the central screw 70, said central screw 70 is translated towards the first rear side 16 of the substantially hollow body 10, as the outer screw thread 76 is engaged with the first threaded through bore 18. This translation leads to a movement of the ball head 72 within the tracks 55, 56 of the cylindrical channel 54. As these tracks 55, 56 include an acute angle in relation to the central axis of the first threaded through bore 18, the motion of the ball head 72 along said tracks 55, 56 imparts a motion of the second body 40 relative to the first body 10. As the second portion 131 of strut 17 is received within the guiding bore 132, this movement is guided in a linear anterior to posterior direction.

Simultaneously, the driving tip 77 of the central screw 70 presses against the angled slope 52 hence supporting the force transfer from the linear translation of the central screw 70 to the motion of the bodies 10, 40 relative to each other.

As a result, the second body 40 is pushed out of the first body 10 towards the second, expanded configuration.

Upon unscrewing of the central screw 70, the central screw 70 travels towards the first front side 15 of the first body 10. The ball-head 72 is engaged in tracks 55, 56 and hence will pull the second body 40 back into the first body 10. Inter-operatively the expandable spinal implant can also be collapsed when necessary.

Figure 9:
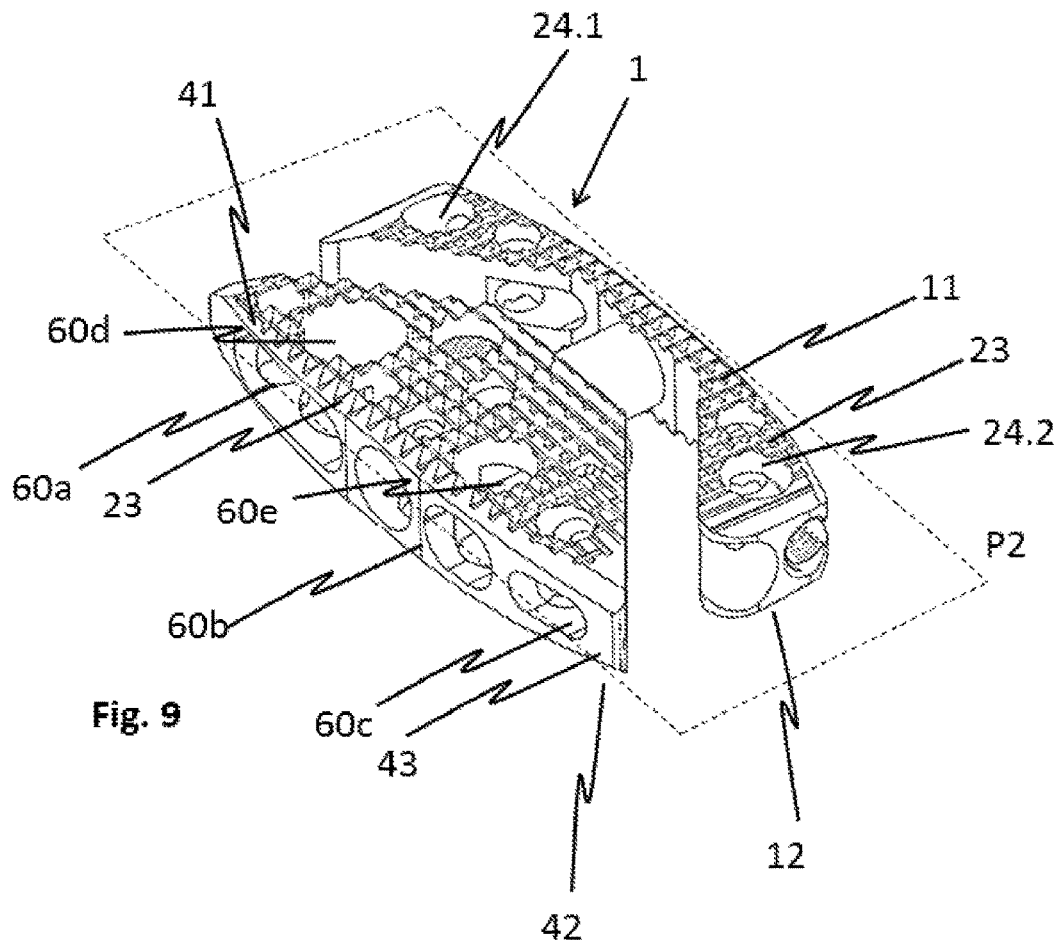
FIG. 9 the expandable implant assembly including rough structures.

Referring to FIG. 9, the expandable spinal implant assembly 1 is shown in an expanded configuration. The first endplates 11, 12 comprise teeth 23 or another rough structure for primary fixation by friction with the vertebral bodies once implanted. Further, one or more pockets 24.1, 24.2 are provided in each of said first endplates 11, 12 to allow for bone-graft placement and bone in-growth. The second body 40 comprises multiple pockets 60a-60z for bone-graft placement and bone in-growth. Said pockets 60a-60z are located at the second anterior end 43 as well as the second superior endplate 41 and the second inferior endplate 42. Also the second endplates 41 and 42 comprise teeth 23 or another rough structure for primary fixation by friction.

Furthermore the expandable spinal implant assembly comprises a central plane P2 and is designed symmetrically in relation to this plane. Due to this symmetry the second body 40 may be used in two orientations, i.e. flipped in relation to the second central plane P2.

Figure 10:
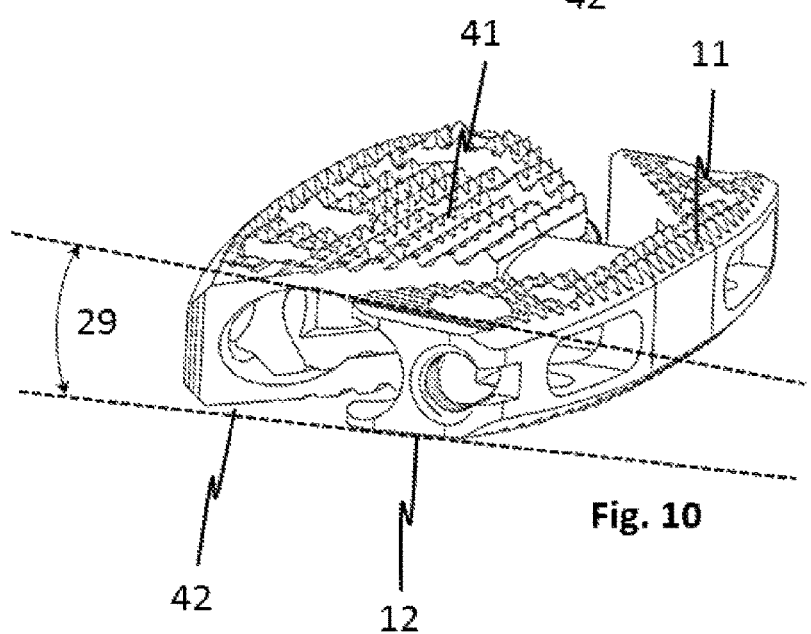
FIG. 10 the expandable implant assembly comprising a lordotic endplate angle.

As shown in FIG. 10, in one embodiment the superior endplates 11, 41 and the inferior endplates 12, 42 are arranged relative to each other under a first inclination angle 29. The first inclination angle 29 is chosen such as to match the lordotic curve of the natural spine. The inclination angle may thus vary from 3° to 20°, preferably from 8° to 10°. In an alternative embodiment said endplates are parallel, in other words, having an inclination angle of 0°.

Figure 11A:
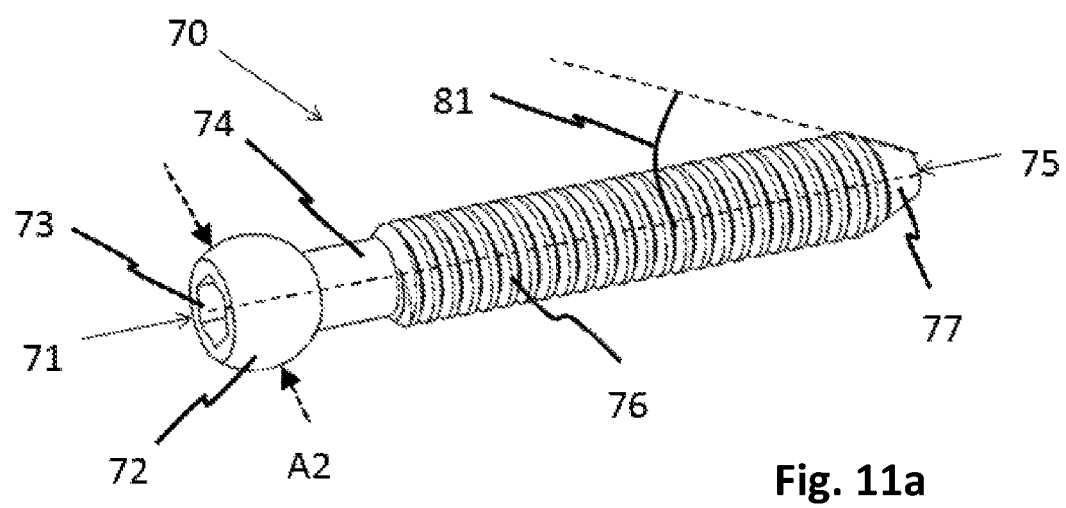
FIG. 11a-11d different embodiments of the central screw.

FIG. 11a shows the central screw 70 in greater detail. The central screw 70 comprises a first end 71 with a ball-head 72. The ball-head 72 includes a drive 73. Said ball-head 72 has a second diameter A2 which is substantially equal to the first diameter A1 of the cylindrical channel 54 of the second body 40. The central screw 70 furthermore comprises an elongated shaft 74 extending from said first end 71 to a second end 75.

The elongated shaft 74 is a threaded shaft having an outer screw thread 76 extending from said ball-head 72 to said second end 75. In an alternative embodiment the said outer screw thread 76 is a screw thread with a double or triple lead to facilitate a larger translation per turn. The elongated shaft 74 has a third diameter A3. The central screw 70 has a third length L3. The third length L3 spans the entire elongated shaft 74 as well as the ball-head 72. In one example, the ratio between the second diameter A2 and the third diameter A3 is larger than 110:100, or more specifically larger than 130:100. With a large ratio between the second diameter A2 and the third diameter A3 the transfer of translational forces between the central screw 70 and the cylindrical channel 54 is enhanced.

The ratio between the first length L1 of the expandable spinal implant assembly 1 and the third length L3 of the central screw 70 may be smaller than 100:80, and more specifically smaller than 100:70.

The second end 75 preferably comprises a driving tip 77. Said driving tip 77 is sized and shaped to engage with said angled slope 52. In one example the driving tip 77 is conical and has a fourth angle 81 which is substantially equal to the third inclination angle 62 of said angled slope 52 of the substantially hollow second body 40. In another example the driving tip 77 has a substantially spherical shape or comprises a radius.

Figure 11B:
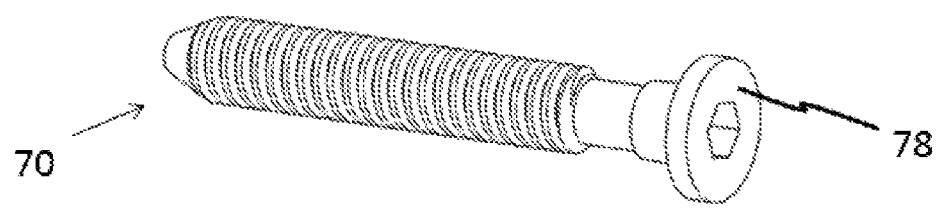
Figure 11C:
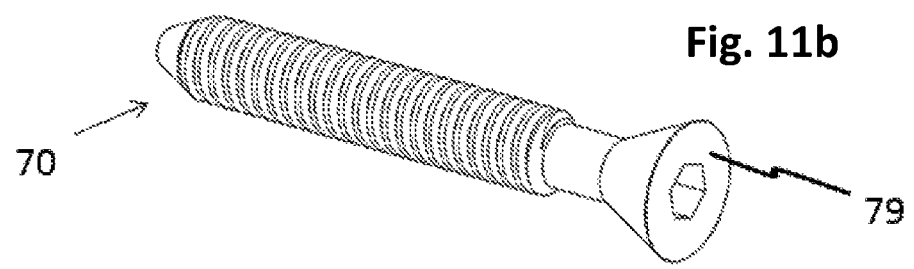
Figure 11D:
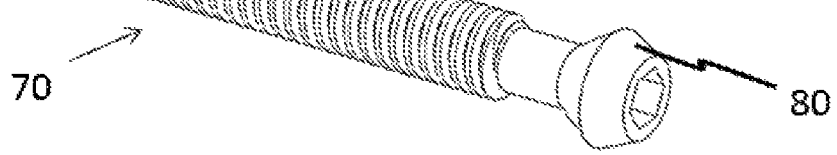

FIGS. 11b to 11d depict alternative designs of the central screw 70, namely comprising a cylindrical head 78, a conical head 79 or a double conical head 80.

FIGS. 12a and 12b show an insertion instrument 100 used in connection with an expandable spinal implant assembly 1 according to the present invention. The insertion instrument 100 comprises two central channels 101, 102. The first central channel 101 is configured to guide a screwdriver 110 for actuation of the central screw 70. The second central channel 102 is intended to guide a coupling core 115. The coupling core 115 comprises a threaded tip 116 for engagement into the second threaded through bore 19 of the first body 10. The insertion instrument 100 furthermore comprises a nose 103. The nose 103 is configured to engage with the recess 22 of the first body 10. By simultaneous engagement of the nose 103 into the recess 22 and the engagement of the coupling core 115 into the second threaded through bore 19, the expandable spinal implant assembly 1 is coupled to the insertion instrument 100.

Figure 13A:
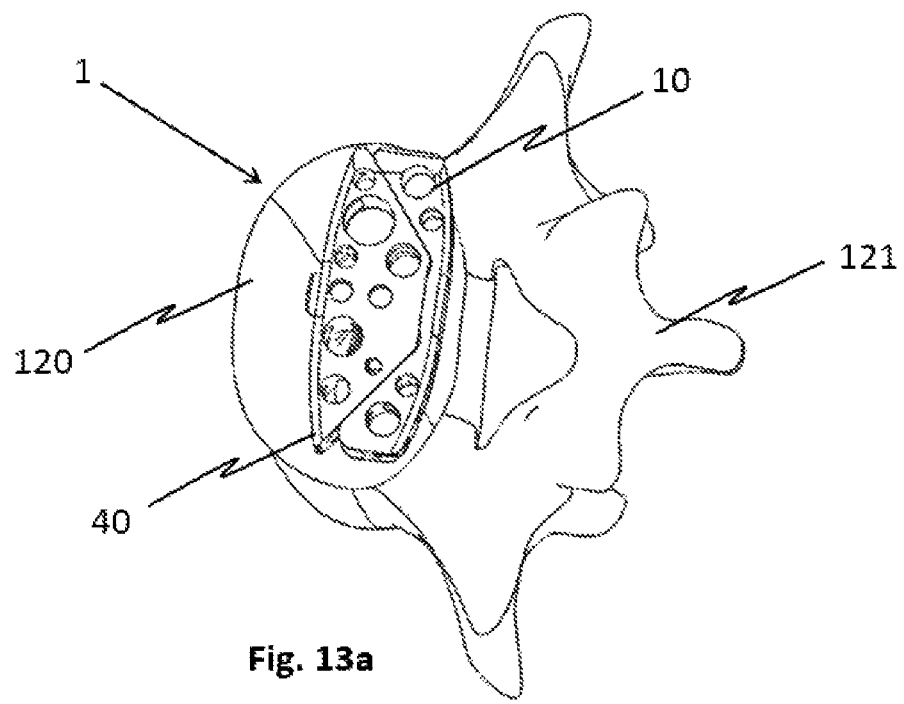
FIGS. 13a, 13b the second embodiment arranged on a vertebral body.
Figure 13B:
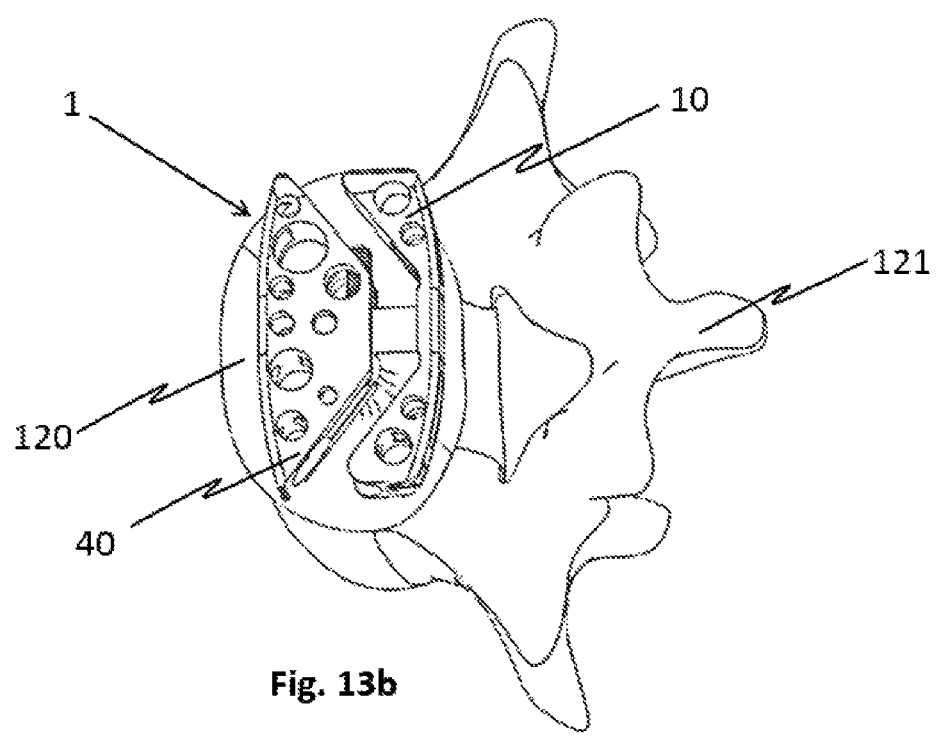

FIGS. 13a and 13b show the expandable spinal implant 1 arranged on a vertebral body 121 of a target vertebra 120 in a schematic representation. For reasons of simplicity, only one vertebra 120 is shown. However, a person having skill in the art recognizes that the expandable spinal implant 1 would be arranged between two vertebrae in replacement to an intervertebral disc. FIG. 13a shows the expandable spinal implant in the first, collapsed or unexpanded configuration where the expandable spinal implant assembly 1 has a first footprint on the vertebral body 121. FIG. 13b shows the expandable spinal implant assembly 1 in the second, expanded configuration having an increased footprint on said vertebral body 121. This increased footprint is due to the relative motion of the second body 40 relative to the first body 10 in a posterior to anterior direction.

The invention claimed is:

1. An expandable spinal implant assembly for insertion between two adjacent vertebral bodies, comprising:
    a) a first body with a first superior endplate and a first inferior endplate;
    b) at least one strut extending from or within the first body, and being connected with the first superior endplate and first inferior endplate, the strut comprising a first threaded through bore with a central axis;
    c) a substantially hollow second body with a second superior endplate and a second inferior endplate, the substantially hollow second body being at least partially engaged with the first body;
    d) a central screw with a first end comprising a ball-head and a drive, the central screw further having a threaded shaft which is arranged to be engaged within the first threaded through bore; wherein
        at least one track is arranged on a top inside face of the second superior endplate and/or on a bottom inside face of the second inferior endplate, the at least one track being oriented at an acute angle relative to the central axis of the first threaded through bore when the substantially hollow second body is at least partially engaged with the first body, wherein the ball-head of the central screw is engaged in the at least one track, and wherein a surface roughness of at least one of the ball-head, threaded shaft or at least one track is at most 25 micrometers.

2. The expandable spinal implant assembly according to claim 1, wherein the surface roughness is at most 5 micrometers, or more specifically at most 0.8 micrometers.

3. The expandable spinal implant assembly according to claim 1, wherein the expandable spinal implant assembly includes a superior track located on the top inside face of the second superior endplate, and an inferior track located on a lower inside face of the second inferior endplate, the superior track and the inferior track being arranged substantially symmetrically to each other and forming a cylindrical channel.

4. The expandable spinal implant assembly according to claim 1, wherein the acute angle of the at least one track relative to the central axis of the first threaded through bore is between 5 degrees and 45 degrees, or more specifically between 10 degrees and 30 degrees.

5. The expandable spinal implant assembly according to claim 1, wherein a first front side of the first body comprises a recess and a second threaded through bore, the recess being arranged substantially parallel to a second central axis of the second through bore for forming an angle stable connection means with an insertion instrument.

6. The expandable spinal implant assembly according to claim 1, wherein a ball head of the central screw is a cylindrical head, a conical head or a double conical head.

7. The expandable spinal implant assembly according to claim 1, wherein the strut comprises a first portion connected with at least one of the first superior endplate and first inferior endplate, and a second portion of cylindrical shape extending from the first portion, and wherein the substantially hollow second body comprises a guiding bore sized and shaped to receive the second portion.

8. The expandable spinal implant assembly according to claim 7, wherein the second portion is of a substantially rectangular or oblong shape, and the substantially hollow second body comprises a guiding channel sized and shaped to receive the second portion of the strut.

9. The expandable spinal implant assembly according to claim 1, wherein a ball head has a ball head diameter and the elongated shaft has a shaft diameter, and wherein a ratio between the ball head diameter and the shaft diameter is at least 110:100, or more specifically at least 130:100.

10. The expandable spinal implant assembly according to claim 1, wherein the expandable spinal implant assembly has an assembly length and the central screw has a central screw length, wherein a ratio between the assembly length and the central screw length is smaller than 100:80, or more specifically smaller than 100:70.

11. The expandable spinal implant assembly according to claim 1, wherein the at least one of the endplates comprises a porous and rough structure, sized and shaped to allow for bone in-growth of a vertebral body.

12. The expandable spinal implant assembly according to claim 1, wherein the central screw while being engaged inside the first threaded through bore, is seated against at least one of the tracks and inside faces such that the central screw is arranged to inhibit rotation of the first body in relation to the substantially hollow second body.

13. A method for spinal fusion, the method comprising:
 a) removing an intervertebral disc between two adjacent vertebrae;
 b) placing of an expendable spinal implant assembly according to claim 1 between the two adjacent vertebrae in a first, unexpanded configuration, the expendable spinal implant assembly having a first footprint in the first, unexpanded configuration; and
 c) expanding the expendable spinal implant assembly to a second, expanded configuration having a second footprint which is larger than the first footprint by rotating the central screw.

14. The method according to claim 13, wherein a placement of the expandable spinal implant assembly is performed using an insertion instrument which is coupled to the expandable spinal implant assembly via a threaded tip of a coupling core of the insertion instrument threadably engaged with a second through bore of the expandable spinal implant assembly.

* * * * *